(12) United States Patent
Alshomer et al.

(10) Patent No.: US 9,579,098 B2
(45) Date of Patent: Feb. 28, 2017

(54) BENDABLE SUTURE NEEDLE WITH FREE VARYING ANGLE AND HOLDER THEREFOR

(71) Applicant: King Saud University, Riyadh (SA)

(72) Inventors: Feras M. Alshomer, Riyadh (SA); Abdulaziz Alshail, Riyadh (SA)

(73) Assignee: King Saud University, Riyadh (SA)

(*) Notice: Subject to any disclaimer, the term of this patent is extended or adjusted under 35 U.S.C. 154(b) by 904 days.

(21) Appl. No.: 13/835,702

(22) Filed: Mar. 15, 2013

(65) Prior Publication Data

US 2014/0277109 A1 Sep. 18, 2014

(51) Int. Cl.
*A61B 17/06* (2006.01)
*A61B 17/062* (2006.01)
(Continued)

(52) U.S. Cl.
CPC .... *A61B 17/0625* (2013.01); *A61B 17/06066* (2013.01); *A61B 17/0469* (2013.01);
(Continued)

(58) Field of Classification Search
CPC .............. A61B 17/06; A61B 17/06061; A61B 17/06066; A61B 17/062; A61B 17/0625; A61B 17/0469; A61B 17/28; A61B 17/2804; A61B 17/29; A61B 2017/06052; A61B 2017/06071; A61B 2017/0608; A61B 2017/06095; A61B 2017/061;
(Continued)

(56) References Cited

U.S. PATENT DOCUMENTS 2,323,183 A * 6/1943 Alleyne ................. A61B 17/28
606/119
5,074,874 A 12/1991 Yoon et al.
(Continued)

FOREIGN PATENT DOCUMENTS

AU 2003235030 A1 3/2005
CN 200987689 Y 12/2007
(Continued)

OTHER PUBLICATIONS

Hu, B et al., "Eagle Claw II: A novel endosuture device that uses a curved needle for major arterial bleeding: a bench study," Gastrointest Endosc. Aug. 2005; 62(2):266-70.
(Continued)

*Primary Examiner* — Todd J Scherbel
(74) *Attorney, Agent, or Firm* — Hauptman Ham, LLP

(57) ABSTRACT

A suturing device including an outer bendable body and an inner bendable needle with a freely bendable angle includes a longitudinally extending outer hollow body having a point and a hollow passage and an inner needle portion or part disposed therein. The outer hollow body is constructed and dimensioned to receive a sized suture needle within the hollow passage with slightly close tolerances welded at its base to a point along the hollow body of the outer part and wherein the outer body includes a lower relatively stiff bendable material and an upper portion of relatively malleable material adjacent to and fixed to the lower portion. Further, the outer hollow body is more malleable as it becomes closer to the point.

4 Claims, 8 Drawing Sheets

(51) Int. Cl.
*A61B 17/29* (2006.01)
*A61B 17/04* (2006.01)
*A61B 17/28* (2006.01)

(52) U.S. Cl.
CPC ........... *A61B 17/28* (2013.01); *A61B 17/2804* (2013.01); *A61B 17/29* (2013.01); *A61B 2017/047* (2013.01); *A61B 2017/06095* (2013.01); *A61B 2017/2901* (2013.01); *A61B 2017/2906* (2013.01); *A61B 2017/2938* (2013.01)

(58) Field of Classification Search
CPC ...... A61B 2017/047; A61B 2017/2901; A61B 2017/2906; A61B 2017/2938
See application file for complete search history.

(56) References Cited

U.S. PATENT DOCUMENTS

| | | | | |
|---|---|---|---|---|
| 5,129,558 | A | * | 7/1992 | Feuerman ............... D05B 87/00 223/102 |
| 5,147,373 | A | * | 9/1992 | Ferzli ................. A61B 17/0469 606/144 |
| 5,250,054 | A | | 10/1993 | Li |
| 6,991,635 | B2 | | 1/2006 | Takamoto et al. |
| 7,063,710 | B2 | | 6/2006 | Takamoto et al. |
| 7,758,597 | B1 | | 7/2010 | Tran et al. |
| 7,875,041 | B2 | | 1/2011 | Mikkaichi et al. |
| 2008/0097347 | A1 | * | 4/2008 | Arvanaghi ......... A61B 10/0233 604/264 |

FOREIGN PATENT DOCUMENTS

| | | |
|---|---|---|
| JP | 3150576 U | 5/2009 |
| JP | 2010154961 A | 7/2010 |

OTHER PUBLICATIONS

McGowan, A., "Closing the Gap," Surgical Products Magazine.
EndoEVOLUTION, "The Most Cost-Effective, Advanced Automated Suturing Devices for Minimally-Invasive Surgery," Endo360 Surgical, http://www.endo360surgical.com/.
Coviden Surgical Solutions, http://www.covidien.com/autosuture/pages.aspx?page=Products/40396.
Wikipedia, the free encyclopedia, http://en.wikipedia.org/wiki/Surgical_suture.
Ethicon Endo-Surgery, EES Product Catalog 2010, http://www.ees.com/Clinician/Product/endodevices/needleholders.

* cited by examiner

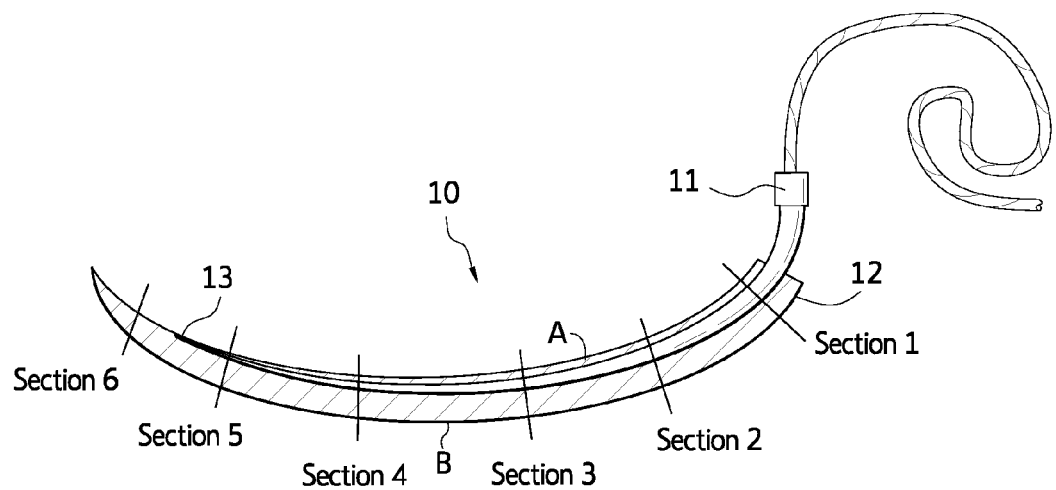
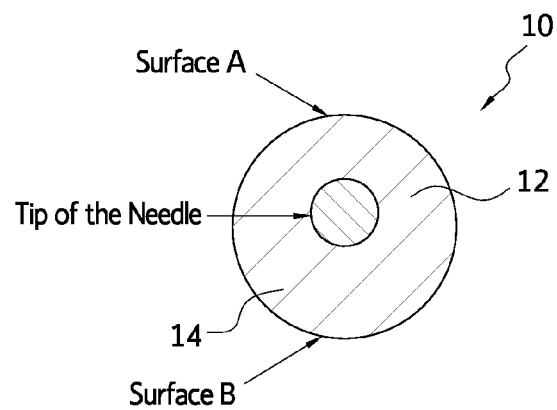 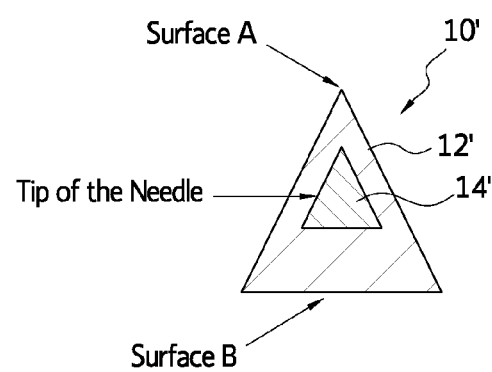
FIG. 1
FIG. 2
FIG. 3

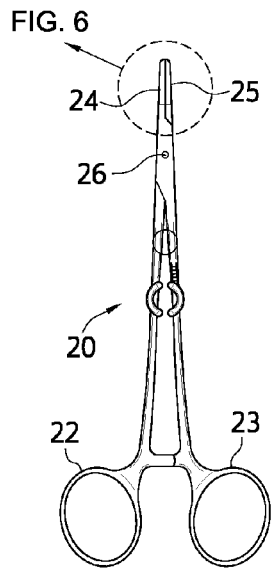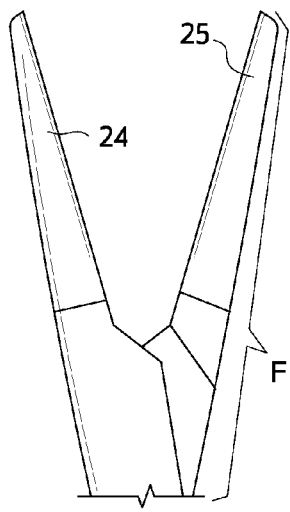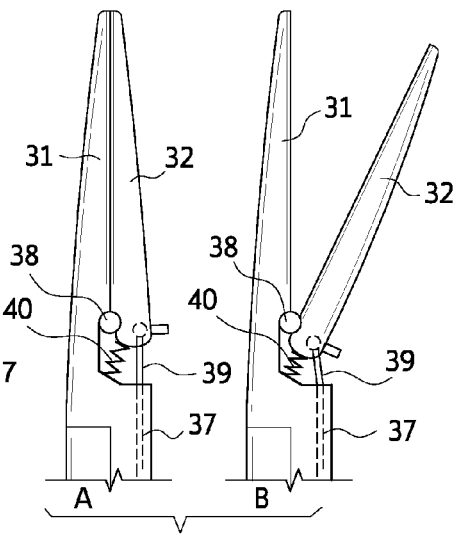
FIG. 5  FIG. 6  FIG. 7
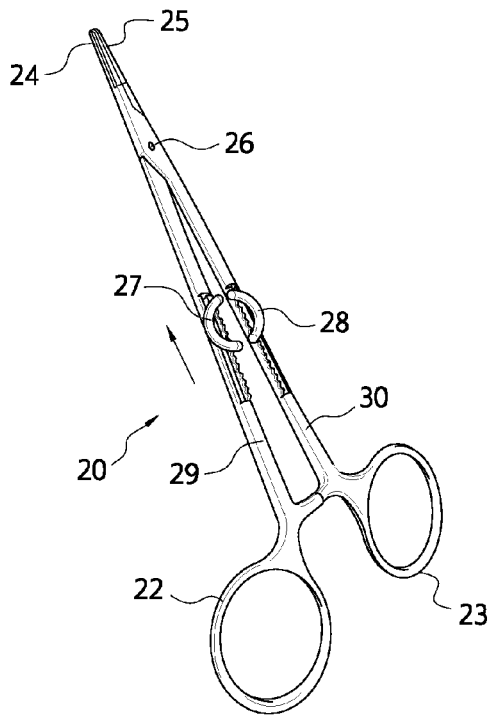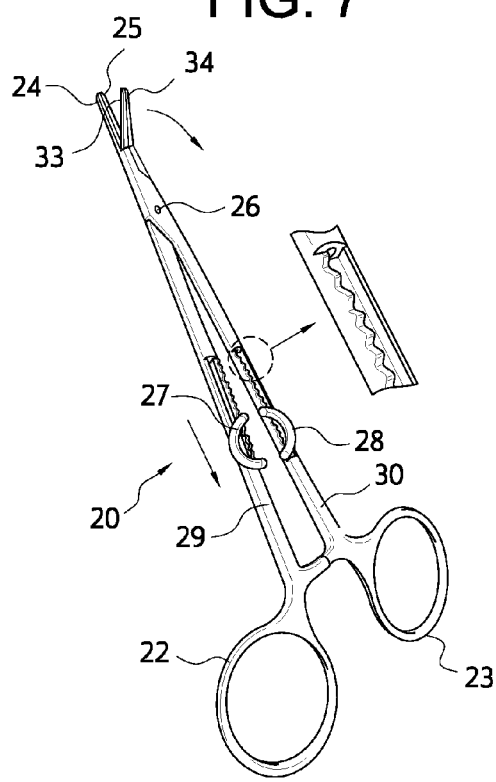
FIG. 8  FIG. 9

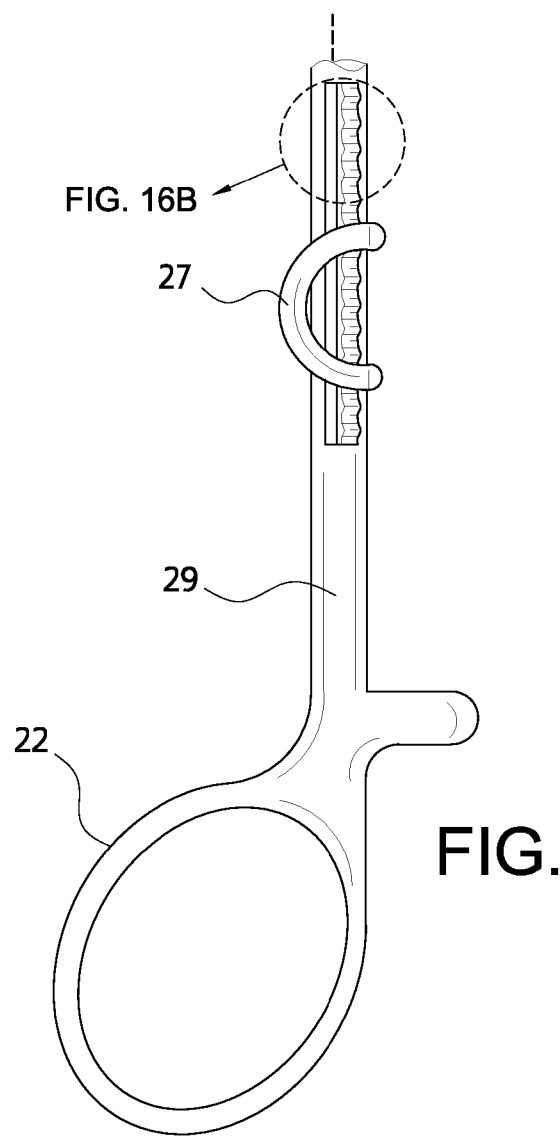
FIG. 16A
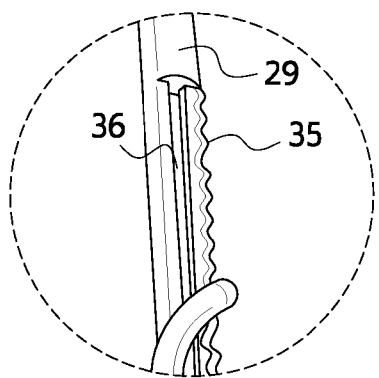
FIG. 16B
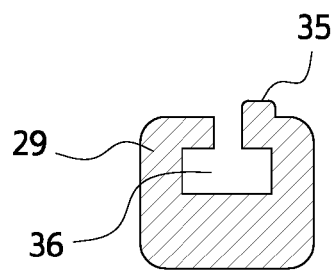
FIG. 16C1
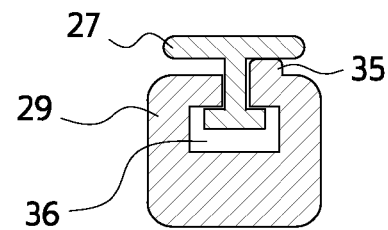
FIG. 16C2

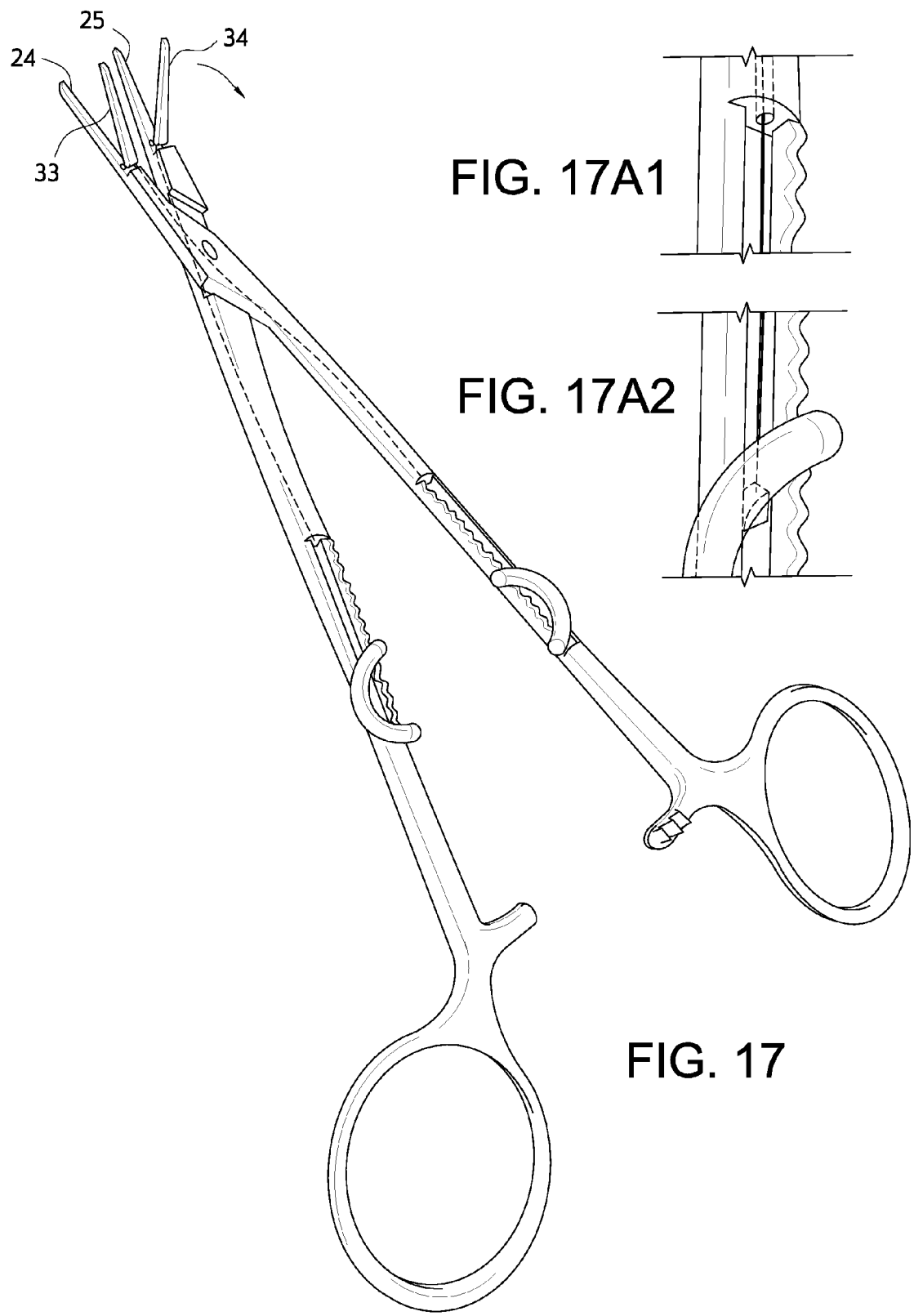

BENDABLE SUTURE NEEDLE WITH FREE VARYING ANGLE AND HOLDER THEREFOR

FIELD OF THE INVENTION

This invention relates to a suturing device and more particularly to a suturing device that includes a bendable outer body and a bendable inner needle with a freely bendable angle. The invention also relates to a modified holder for the suturing device.

BACKGROUND FOR THE INVENTION

Suture needles are well known and have been in widespread use for many years. Such needles come in various sizes and shapes. For example, needles in various sizes are available in straight, ¼ circle, ⅜ circle, ½ circle, ⅝ circle, compound curves and half curved at both ends of a straight segment. Eyed or reusable needles are needles with holes or eyes which are supplied separate from the suture thread. The suture is threaded on site. An advantage is that any thread or needle combination is possible. Swaged or atraumatic needles with sutures comprise a pre-packaged eyeless needle attached to a specific length of thread. With these needles, the doctor or nurse does not have to take time threading the suture which may be difficult with very fine needles and threads.

Suture devices for endoscopic, laparoscopic and intracardiac procedures and the like are also well known. For example, a Li U.S. Pat. No. 5,250,054 discloses an apparatus and method for tying knots in sutures at an interior surgical site. The apparatus comprises an elongated hollow member having a distal portion extending at an acute angle to the major longitudinal axis of the hollow member and terminating in a distal end surface, and a rod being partly flexible along its length and having a J-shaped hook at its distal end, wherein the hook is sized to grapple the suture which is to be manipulated by the device. The rod is received within the interior of the hollow member and adapted to reciprocate relative to the hollow member so that the hook can be moved between (i) an extended position wherein the mouth of the hook is spaced from the distal end surface of the hollow member by more than the thickness of the suture, whereby the suture can be grappled by the hook, (ii) an intermediate position wherein the mouth of the hook is spaced from the distal end surface of the hollow member by less than the thickness of the suture, but the interior base of the hook is spaced from the distal end surface of the hollow member by more than the thickness of the suture, whereby a suture grappled by the hook will be slidably captured to the hollow member, and (iii) a withdrawn position wherein the interior base of the hook is spaced from the distal end surface of the hollow member by less than the thickness of the suture, whereby a suture grappled by the hook will be fixedly captured to the hollow member.

A more recent patent of Tran et al. U.S. Pat. No. 7,758,597 discloses a suturing instrument and method for placing mattress stitches in soft tissues. An elongated shaft with a stationary jaw and a moveable jaw is disposed at the distal end and is coupled to a handle grip at the proximal end and is configured to manipulate the jaws into open and closed positions. The jaws are configured to allow for atraumatic grasping of soft tissues. The stationary jaw is comprised of a serrated face incorporating apertures through which needles attached to opposite ends of a single strand of suture material may be driven out into and through grasped tissue. The serrated upper jaw is configured with needle catch adapted to accept and capture the needles and suture. The handle is released to open the moveable jaw, the instrument may be withdrawn, trailing the suture, and leaving a mattress stitch in the grasped tissue.

Notwithstanding the above, it is presently believed that there is a need and a potential market for a suturing device in accordance with the present invention. There should be a market for such devices to facilitate bending a needle when a surgeon feels a need to bend a suture needle to a certain angle to give them more freedom to do their work. In many cases, when space allows, movement force is applied using ones fingers to bend the needle. This is done by holding the two ends of the needle and by applying some degree of force according to the size of the needle and the manufactured angle to induce a bend. At times and for very fine small caliber needles the actions might affect the strength of the needle and cause the needle to break or to make the needle more malleable and too weak to penetrate certain tissue. Also, in certain areas like in the case of laparoscopic or endoscopic surgery, it is difficult without the presently disclosed device to accomplish a change in an angle.

SUMMARY OF THE INVENTION

In essence, the present invention contemplates a suturing device that includes a bendable outer body and bendable inner needle with a freely bendable angle. The suturing device comprises and/or consists of a longitudinally extending outer hollow body having a point and a hollow passage extending through the hollow body. The device also includes a sized suture needle having a point at one end and wherein the longitudinally extending outer hollow body is constructed and dimensioned to receive a suture needle within the hollow passage with close tolerances and with a point of the suture needle fixed to the outer hollow body. The hollow outer body includes a lower relatively stiff bendable material and an upper portion of relatively malleable material adjacent to and fixed to the lower portion and wherein the outer body is more malleable as it comes closer to the point. The malleableness may be controlled by the thickness of the stainless steel body and/or by varying the composition of an alloy.

In a preferred embodiment of the invention, a suturing device as described above further comprises: a holder and a handle for manipulating the holder and a pair of forwardly extending arms and each of the arms includes a pair of gripping jaws. For example, arm one has first and second gripping jaws i.e. a first fixed jaw and a second movable jaw pivotally connected together. The second arm also has a pair of jaws, namely a third fixed jaw and a fourth movable jaw pivotally connected to the third fixed jaw to provide two clamps. The first pair of jaws is for attachment to a relatively stiff portion or lower portion of the outer housing while the second pair of jaws namely a movable second jaw and a movable jaw four are fixed to an outer rear portion of the inner part.

In the preferred embodiment of the invention, the suturing device further comprises or consists of a pivot and a pair of longitudinally extending arms pivotally connected by the pivot at an intermediate portion thereof. Further, a pair of handles and a pair of arc shaped elements are on one side of the pivot. As a key element in the preferred embodiment, the two opposing arc shaped elements are part of an integrated pulling system in which the arc shaped elements are connected to the second movable and fourth movable jaws on each extending arm through an integrated cable within a body of each extending arm. For example, a first arc shaped element is connected by an integrated pulling system within a body of the forwardly extending first arm through a second hinge point to the second movable jaw of the first extending arm.

The invention will now be described in connection with the accompanying drawings wherein like parts are identified with like members.

DESCRIPTION OF THE DRAWINGS

FIG. 1 is a schematic side view of a suturing device in accordance with the present invention divided into six sections;

FIG. 2 is a schematic cross-sectional view of a first embodiment of the invention taken at about section 5 of FIG. 1 and wherein the suture needle has a circular cross section;

FIG. 3 is a cross-sectional view of a second embodiment of the invention taken at about section 5 of FIG. 1 and wherein the suturing device inclusive of the needle have a triangular cross section;

FIG. 5 is a schematic illustration of a needle holder in a closed position in accordance with one embodiment of the invention;

FIG. 6 is a schematic illustration of two arms of the holder shown in FIG. 5;

FIG. 7 is a schematic illustration of one side of the holder's front and back arms with an integrated connecting cable or wire attached to the moveable part of the holder and a spring for returning a jaw to its clamping position i.e. first fixed jaw and second movable jaw of the first extending arm;

FIG. 8 is a schematic illustration of a needle holder in a closed position with an arrow indicating the pulling direction of a cable for opening the jaws;

FIG. 9 is a schematic illustration of the instrument after pulling a connecting cable or wire;

FIGS. 16A, 16B, 16C1 and 16C2 illustrate a portion of a forwardly extending arm of a modified holder, a cross section of a passageway in one of the forwardly extending arms and an arc-shaped element as it moves with respect to the forwardly extending arms; and FIGS. 17, 17A1 and 17A2 are schematic illustrations of a portion of a forwardly extending arm, a pair of jaws at one end of a forwardly extending arm and an arc-shaped element.

DESCRIPTION OF THE PREFERRED
EMBODIMENTS OF THE INVENTION

Figure 4:
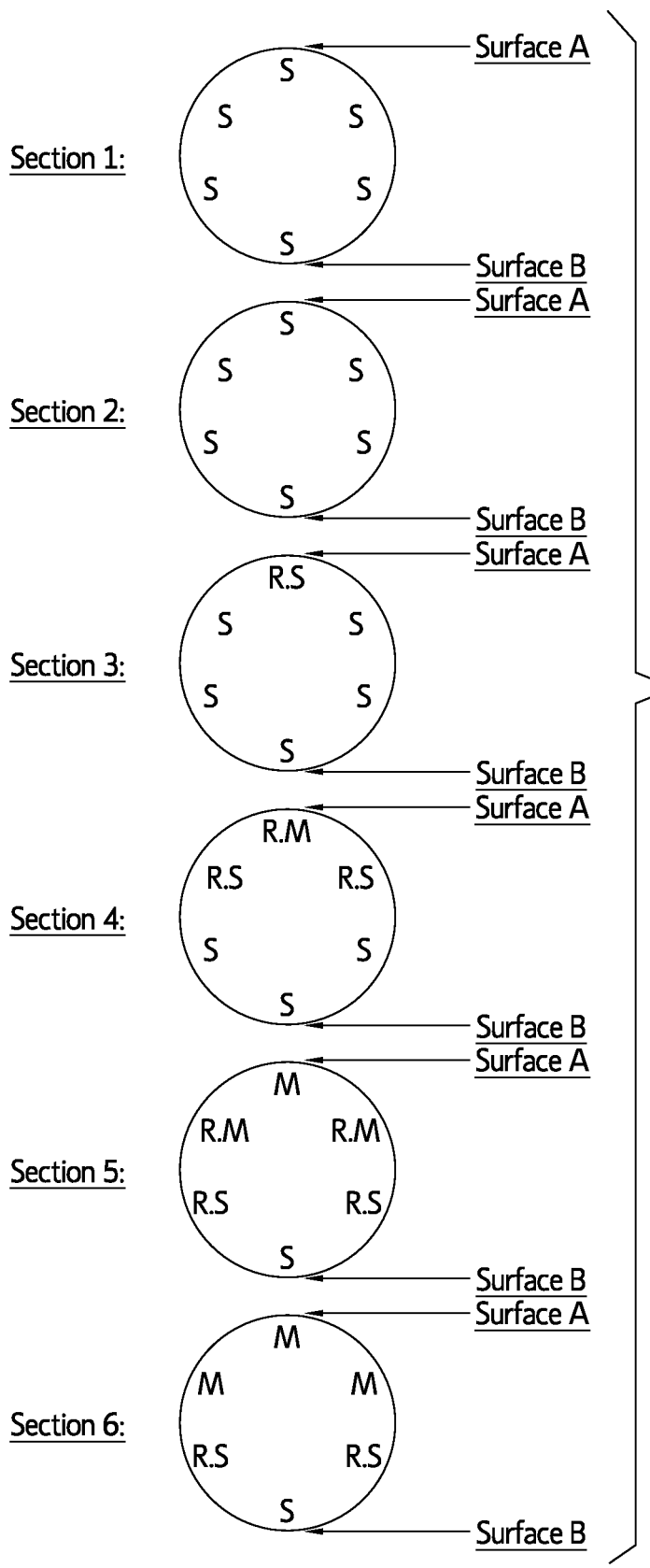
FIG. 4 is a schematic illustration that shows the stiffness, relative stiffness, malleableness and relatively malleableness of various parts at different sections of the surgical device shown in FIG. 1.
Figure 10:
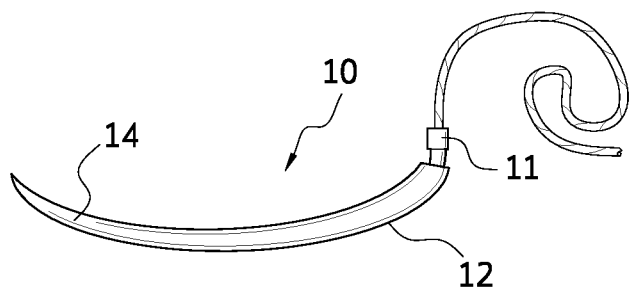
FIG. 10 is a schematic illustration of a modified needle in accordance with the present invention.
Figure 11:
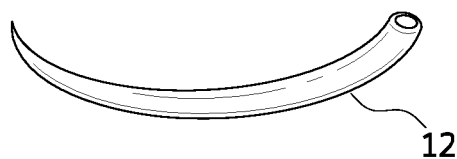
FIG. 11 is a schematic illustration that shows the general layout of part one i.e., the bulky part of a suture device in accordance with the present invention.
Figure 12:
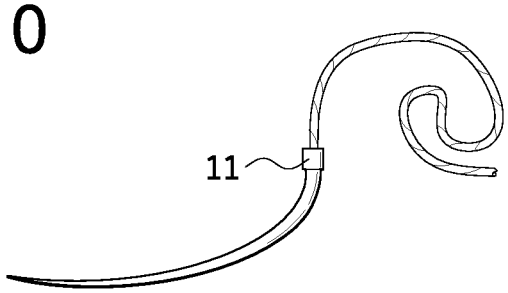
FIG. 12 is a schematic illustration of a needle or part two of the device that fits into part one.

Referring now to FIGS. 1-4, a suturing device 10 in accordance with the present invention includes a hollow outer body 12 and an inner suture needle 14. The suturing device 10 is shown without a holder as will be incorporated in a further embodiment of the invention. At each section 1-6 an overall cross section is shown with an indication of stiffness or malleability in the various positions at each section as illustrated in FIG. 4. FIG. 2 is a schematic cross-sectional view taken from the tip of a suturing device 10 and indicating a top surface A and bottom surface B. As the suturing device proceeds from section 6 to section 1 it is tapered and the stiffness increases and malleability decreases.

Figure 15:
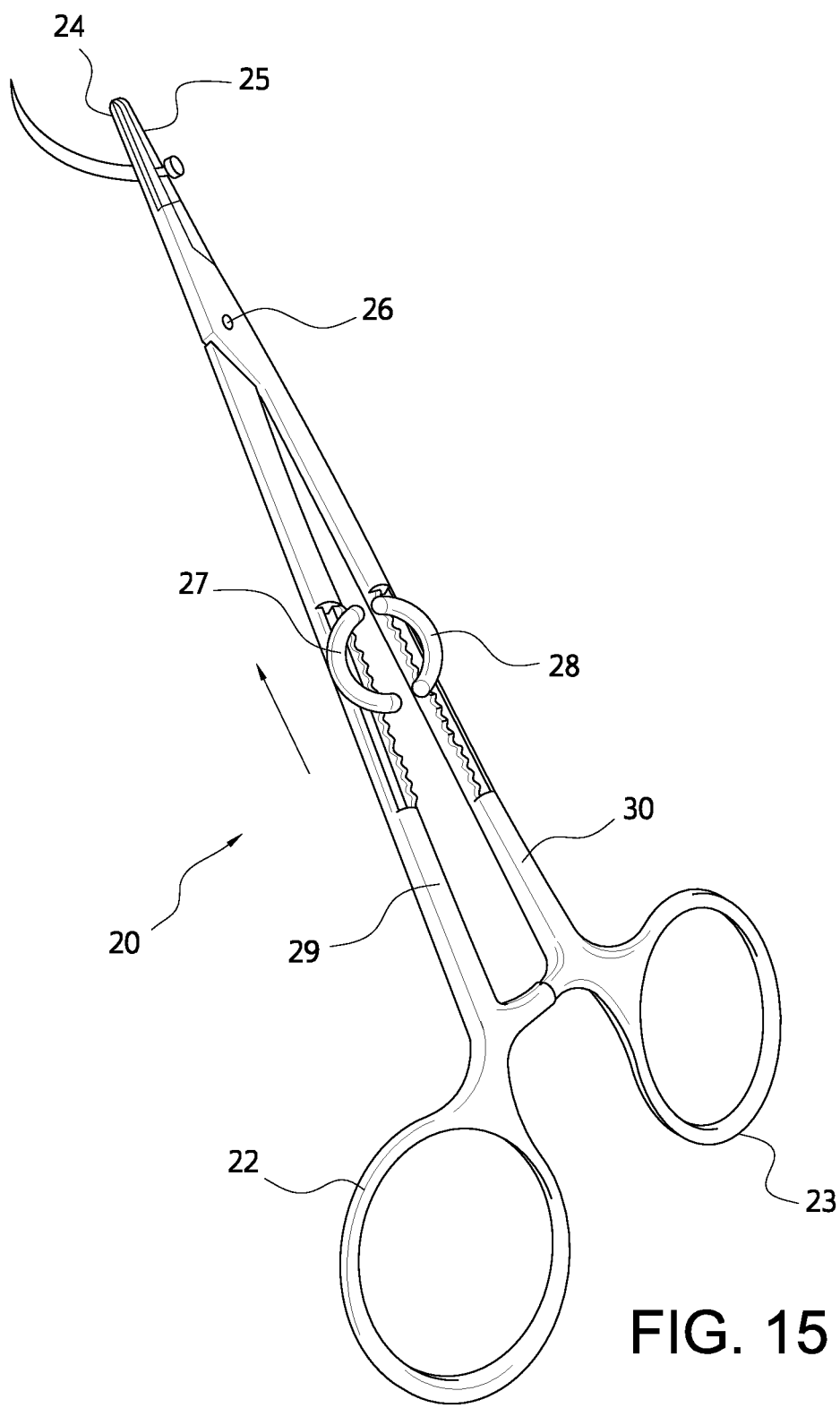
FIGS. 15 and 15A are schematic illustrations of a modified holder in accordance with one embodiment of the invention.
Figure 15A:
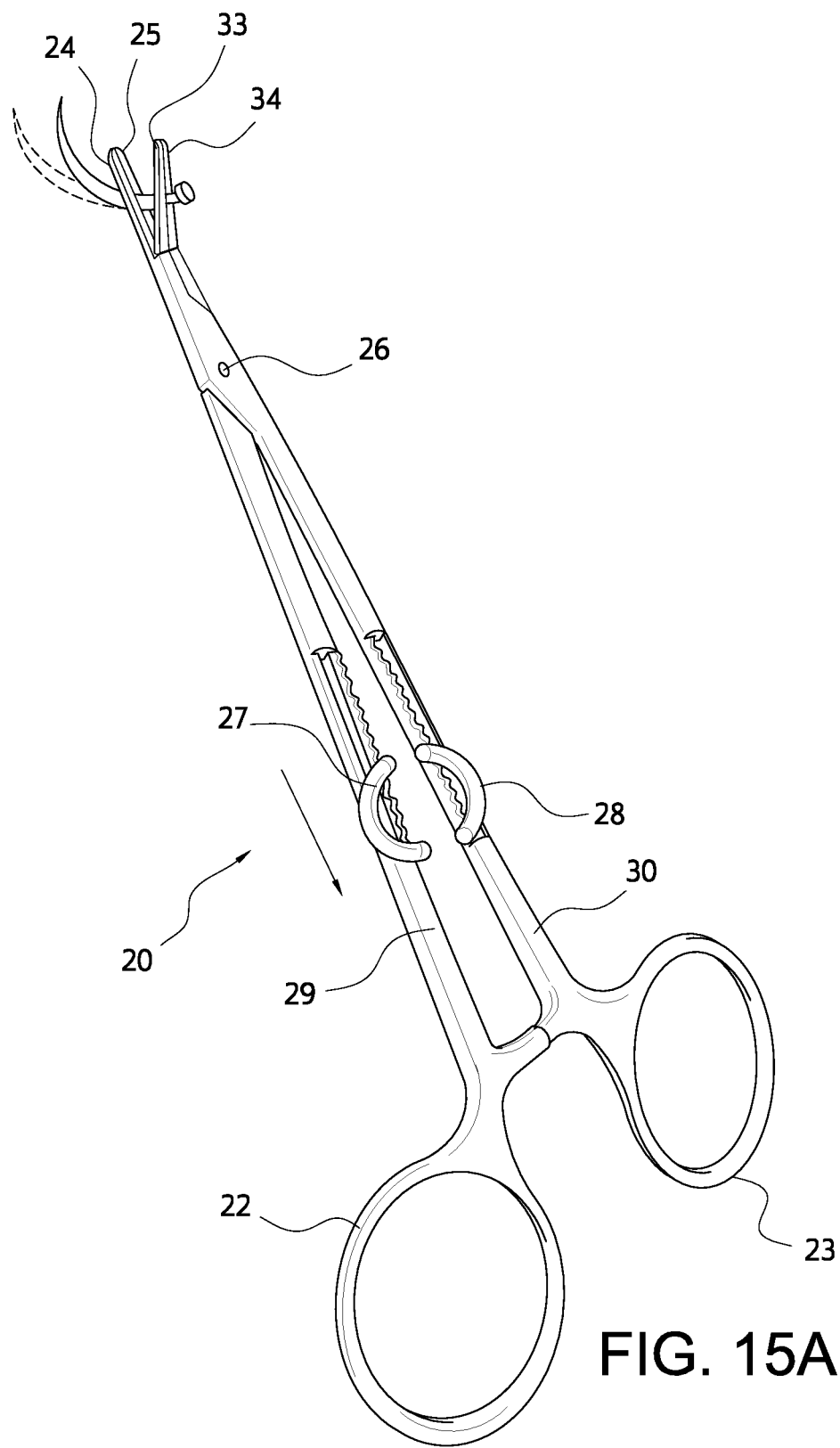

The main function of a modified holder 20 is to hold, position and bend the suturing device 10 to a desired degree. As illustrated, note FIGS. 5, 8 and 9 and particularly FIGS. 15, 16 and 17, the holder 20 resembles a pair of scissor like or medical clamp like instrument. The modified holder 20 includes two forwardly extending arms 29 and 30. These arms each include an inner passageway and a wire or cable extending through the passageway and connected at one end thereof to arc-shaped elements 27 and 28.

Each of the arc-shaped elements 27 and 28 are movable longitudinally along one of the forwardly extending arms 29 and 30 as indicated by an arrow in FIG. 8. Each of the wires are connected at one end to an outer side of one of the pair of jaws and an opposite end to one of the arc-shaped elements 27 and 28. Thus, by pulling on one of the arc-shaped elements will open one of the jaws. As shown in FIG. 9 a spring closes the jaws when released by a slight pull and release of the arc-shaped element in a conventional manner. The extra set of jaws is numbered 33 and 34 over the jaws 24 and 25. A track and conventional spring bias mechanism returns the jaws to a closed position by a slight pull and release of an arc-shaped element.

As more clearly shown in FIGS. 15, 16A-C and 17, the two forwardly extending arms 29 and 30 each include a passageway extending therethrough and a wire or cable within the passageway. The wire or cable is fixed at one end to one of the arc-shaped elements and the other end to a movable spring biased jaw as for example to a protrusion extending outwardly therefrom (see FIG. 7). A spring between a base and a jaw biases the pair into a closed position when the arc-shaped element is released by a surgeon.

The holder 20 includes the arc-shaped elements 27 and 28 wherein each one is located along one forwardly extending arm. Each of the forwardly extending arms of the holder 20 hosts the connecting wires in the longitudinally extending passageway. For example, the path of the pulling on an external move along a longitudinal path of a generally C-shaped guide is shown in FIG. 16A.

FIG. 17 illustrates a single forwardly extending arm that is to be identical with its fellow second forwardly extending pivot 38 a fixed jaw and a movable jaw. Pulling both arc shaped elements simultaneously towards the surgeon, a surgeon will open the movable jaws 33 and 34 used to clamp the rear portion of the inner part of the suturing device.

To be more specific, the extra jaw i.e., the movable portion of the jaws on one arm has its own separate joint or pivot 38 where the jaw moves away from a fixed jaw and pivots away from its counterpart on the same arm.

It is also contemplated that the suturing device 10 may have a triangular cross section as indicated in FIG. 3. In such case, the needle, as in the circular embodiment, is tapered from section 1 to section 6 with the tip or sharp point at about section 6.

As illustrated in FIG. 4, the suturing device as illustrated in FIG. 2 or 3 will have essentially the same degree of stiffness and malleability in both embodiments. However, the circular cross section applies to a preferred embodiment and will be referred to hereinafter in describing the invention. As indicated with respect to section 1 the outer body 12 is at its thickest and/or stiffest at a rear point at the rear of the device 10. For example, as shown the device 10 is stiffest at the 12:00 o'clock, 4:00 o'clock, 6:00 o'clock, 8:00 o'clock and 10:00 o'clock positions. The same conditions prevail in section 2.

In section 3, the stiffness in the 12:00 o'clock position is slightly reduced to "relatively stiff" while the stiffness in the 2:00 o'clock, 4:00 o'clock, 6:00 o'clock, 8:00 o'clock and 10:00 o'clock positions remain the same as in section 2. Then, in section 4, the condition of the 12:00 o'clock position is relatively malleable and at the 2:00 o'clock and 10:00 o'clock positions are relatively stiff. As indicated, the condition at the 4:00 o'clock, 6:00 o'clock and 8:00 o'clock positions are indicated as stiff.

Proceeding onto section 5, the indications at 12:00 o'clock are malleable. At 2:00 o'clock and 10:00 o'clock relatively malleable, at 4:00 o'clock and 8:00 o'clock relatively stiff and at 6:00 o'clock stiff. Finally, in section 6 the degree of stiffness are classified at malleable at 10:00 o'clock, 12:00 o'clock and 2:00 o'clock, relatively stiff at 4:00 o'clock and 8:00 o'clock and stiff at 6:00 o'clock. Section 5 and section 6 are about the same except that at section 6 the 10:00 o'clock and 2:00 o'clock positions are more malleable than in section 5.

The above indications are a general approach to explain the increase in thickness or stiffness of an outer hollow body with an inner suture needle disposed therein. The stiffness may be attributed to thickness or composition of the stainless steel alloy or layers of different alloys.

Referring now to FIGS. 5-17, a holder 20 for positioning a suturing device 10 is shown in FIG. 5 and has a general appearance of a pair of scissors or clamp with a pair of handles and a pair of forwardly extending arms on a first side of a pivot 26 and a pair of handles 22 and 23 on an opposite side of the pivot 26. The holder 20 is also shown in FIGS. 8-9 and 15-17.

As shown in FIGS. 5, 8 and 9, a pair of arc-shaped elements 27 and 28 are disposed with one element on each of the arms 29 and 30 for guiding one of the pulling cables inside of an arm. For example, a small L-shaped lever 31' is fixed to each moveable arm and extends to the right to move the movable arm toward an open position as shown in FIG. 6 and FIG. 7B.

As shown in FIGS. 10-14 in the preferred embodiment of the invention, the suture device is manufactured in two parts wherein the inner part fits into the outer part. Part one which is an outer or bulky part contains the leading point of the device or the area of first penetration of the tissue. It is shaped with a slight bend and is to be fixed at a certain point to the other part. The outer part is manufactured with relatively stiff and malleable portions. As shown, the stiff portion is the lower portion and the malleable portion is an upper portion and the two portions are welded together along their sides.

The holder is manufactured with two forwardly extending arms and a pair of jaws attached to each arm. A first fixed pair of jaws 24 and 25 will hold the rear portion of the outer body and the second pair of movable jaws 33 and 34 will hold the rear outer portion of the inner part of the suturing device. Then with each pair of jaws clamped in a closed position, a surgeon's brings the handles of the holder together. To hold the overall suturing device in which the movable jaws of each forwardly extending arms 33 and 34 will hold the rear end of the inner part of the suturing device (11 in FIG. 13) while the other fixed jaws of each forwardly extending arms (24 and 25) will hold the outer bulky part of the suturing device (near 12 in FIG. 13), that the manipulation of the movable jaws through pulling and realizing the two arc shaped elements (27 and 28) simultaneously will result in the displacement of the inner part of the suturing device out of the bulky outer part guided by the amount of pulling force, malleability and point of welding between the two parts and subsequent increase in the degree of bending of the overall suturing device.

Figure 13:
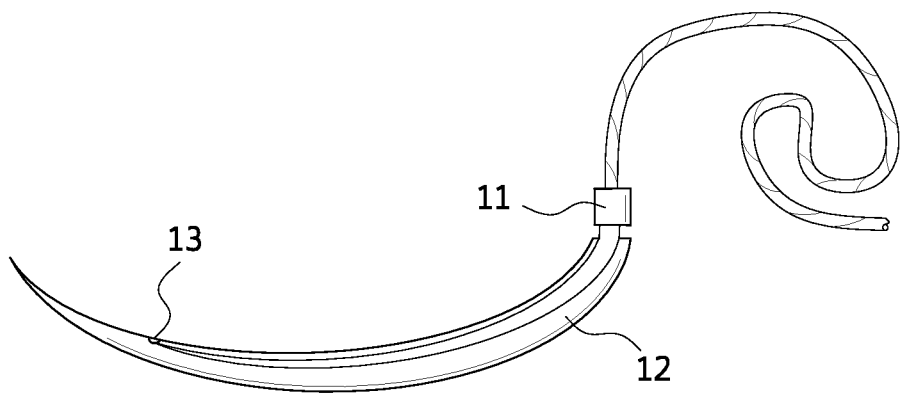
FIG. 13 shows the general layout of the suture device according to the invention including the needle that is welded to part one.
Figure 14:
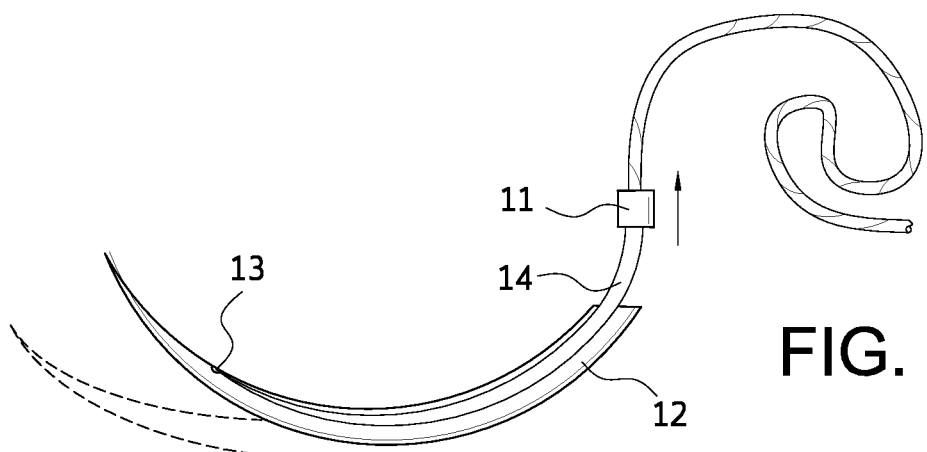
FIG. 14 is a schematic illustration with a needle in different positions as bent by the modified device.

FIG. 13 shows the general layout of the device with both parts fit together and welded to make a single suturing device. FIG. 14 illustrates the needle in different modes of action when the two portions are pulled together using the modified needle holder to induce a preferred angle.

While the invention has been disclosed in connection with its preferred embodiments it should be recognized that changes and modifications may be made therein without departing from the scope of the claims.

What is claimed is:

1. A combination of a suturing device and a holder wherein said suturing device comprises:
   a sized bendable suture needle and a longitudinally extending outer hollow body having a point and a hollow passage therethrough;
   wherein said longitudinally extending outer hollow body being constructed and dimensioned to receive said sized bendable suture needle within said passage with slightly close tolerances; and
   wherein said outer longitudinally extending outer hollow body includes a lower portion of relatively stiff bendable material and an upper portion of relatively malleable material adjacent to and fixed to said lower portion; and
   wherein said longitudinally extending outer hollow body is more malleable as it becomes closer to said point; and
   wherein said holder for said suturing device comprising:
   a pair of forwardly extending arms and means pivotally connecting said forwardly extending arms together intermediate of said forwardly extending arms;
   a pair of handles at one end of said forwardly extending arms with one of said handles on each of said pair of arms on one side of said means pivotally connecting said arms together;
   two pair of spring biased jaws with one of said pair of spring biased jaws disposed at one opposite end of said arm from said handles and in an opposite side of said means pivotally connecting said arms together;
   each of said forwardly extending arms including an arc-shaped element and a longitudinally extending passageway through each of said arms;
   a pair of wires with one of said wires disposed in each of said passageways and connected at one end thereof to one of said arc-shaped elements and at the other end thereof to the one of said pair of jaws and wherein pulling one of said arc-shaped elements toward said handle opens the one of said pair of jaws and releasing said one of said arc-shaped elements closes said one of said pair of jaws due to said spring bias; and
   wherein moving said spring biased jaws simultaneously away from said arms is configured to bend the suturing device held therein by said jaws.

2. A combination of a suturing device and a holder wherein said suturing device consisting of:

a sized bendable suture needle and a longitudinally extending outer hollow body having a point and a hollow passage therethrough;

wherein said longitudinally extending outer hollow body being constructed and dimensioned to receive said sized bendable suture needle within said passage with slightly close tolerances; and wherein said longitudinally extending outer hollow body includes a lower portion of relatively stiff bendable material and an upper portion of relatively malleable material adjacent to and fixed to said lower portion; and wherein said longitudinally extending outer hollow body is more malleable as it becomes closer to said point; and wherein said holder for said suturing device consists of:

a pair of forwardly extending arms and means pivotally connecting said forwardly extending arms together intermediate of said forwardly extending arms;

a pair of handles at one end of said forwardly extending arms with one of said handles on each of said pair of arms on one side of said means pivotally connecting said arms together;

two pair of spring biased jaws with one of said pair of spring biased jaws disposed at one opposite end of said arm from said handles and in an opposite side of said means pivotally connecting said arms together;

each of said forwardly extending arms including an arc-shaped element and a longitudinally extending passageway through each of said arms;

a pair of wires with one of said wires disposed in each of said passageways and connected at one end thereof to one of said arc-shaped elements and at the other end thereof to the one of said pair of jaws and wherein pulling one of said arc-shaped elements toward said handle opens the one of said pair of jaws and releasing said one of said arc-shaped elements closes said one of said pair of jaws due to said spring bias; and wherein moving said spring biased jaws simultaneously away from said arms is configured to bend the suturing device held therein by said jaws.

3. A suturing device comprising:

a sized bendable suture needle with a freely bendable angle and a longitudinally extending bendable outer hollow body having a point and a hollow passage therethrough;

wherein said outer hollow body is constructed and dimensioned to receive said sized bendable suture needle within said passage with slightly close tolerances; and wherein said outer hollow body includes a lower portion of relatively stiff bendable material and an upper portion of relatively malleable material adjacent to and fixed to said lower portion; and wherein said outer hollow body is more malleable as it becomes closer to said point;

wherein said sized suture needle comprises suture needles manufactured in multiple sizes; and in which said suture needles are welded to said outer hollow body at different points to provide various bent angles.

4. The suturing device according to claim 3, in which said various sized suture needles are differentiated by different colors.

* * * * *